United States Patent
Bohon

Patent Number: 5,172,591
Date of Patent: Dec. 22, 1992

[54] OIL WELL SUCKER ROD LOAD MEASUREMENT

[75] Inventor: W. Mark Bohon, Frisco, Tex.

[73] Assignee: Atlantic Richfield Company, Los Angeles, Calif.

[21] Appl. No.: 569,305

[22] Filed: Aug. 20, 1990

[51] Int. Cl.$^5$ .................. E21B 41/00; G01H 5/00; G01N 9/24; G01N 29/18

[52] U.S. Cl. .......................... 73/151; 73/581; 73/597

[58] Field of Search ............ 73/151, 151.5, 581, 73/597

[56] References Cited

U.S. PATENT DOCUMENTS

| | | | |
|---|---|---|---|
| 3,720,098 | 3/1973 | Dixon | 73/597 |
| 3,822,587 | 7/1974 | Makino et al. | 73/581 |
| 3,943,755 | 3/1976 | Arii et al. | 73/597 |
| 3,969,810 | 7/1976 | Pagano | 73/581 |

*Primary Examiner*—Hezron E. Williams
*Assistant Examiner*—George M. Dombroske
*Attorney, Agent, or Firm*—Albert C. Metrailer

[57] ABSTRACT

A load measuring system comprising an acoustic transmitting transducer for injecting an acoustic signal into a load bearing portion of a sucker rod, and receiving transducer for detecting the signal after it passes through a known length of a sucker rod, and a time delay detector for determining the travel time and in turn, the velocity of the acoustic signal. The acoustic velocity is measured in an unloaded portion of the sucket rod to provide a zero load reference. Measurements are then taken in the loaded portion of the rod and used to indicate dynamic load on the sucker rod string.

2 Claims, 3 Drawing Sheets

OIL WELL SUCKER ROD LOAD MEASUREMENT

BACKGROUND OF THE INVENTION

The present invention relates to dynamic measurement of load on an oil well sucker rod pump and, more particularly, to a method and apparatus for measuring the velocity of acoustic waves in both stressed and unstressed portions of the sucker rod in order to determine the level of stress in the stressed portion thereof.

The most common means of artificial lift in oil wells is sucker rod pumping. The basic elements of a sucker rod pumping system are illustrated in FIG. 1. These systems include a prime mover 2, typically an electric motor, which drives a gear box and counterweight unit 4. Gear box 4 in turn drives one end of walking beam 6. The opposite end of walking beam 6 is connected to the upper end of a sucker rod string 8. Sucker rod string 8 extends from the earth's surface to the actual pump 10 located at the bottom of cased well 12.

The major expenses involved in operation of a sucker rod pumping system are the electrical power input needed for motor 2 and expenses of repairing pumps which fail. It is desirable to pump at the highest rate possible to maximize oil production without allowing the pump to go dry which can cause mechanical failure of the pump 10. Various adjustments can be made to the motor speed, counterweight and stroke length to optimize production while minimizing energy use and breakdowns.

The operation of the sucker rod pumping system is optimized using a dynamometer, a device which records load versus displacement during the pumping cycle. The most common dynamometers are mechanical/hydraulic devices. Electronic dynamometers are becoming more common. Electronic dynamometers, especially when coupled with computers, greatly speed analysis. On high production wells, dedicated electronic dynamometers, or pump-off controllers, are sometimes used to continually monitor pumping unit operation, thus assuring maximum performance and minimizing failures.

The primary input to a dynamometer or pump-off controller is the time varying load on the sucker rod string, and in particular, to the polished rod portion positioned at the upper end of the string. Pump-off controllers typically use a permanent electronic load cell attached to the polished rod to measure rod load. These load cells are difficult to install and remove, often resulting in their destruction during workovers. This characteristic also makes them poorly suited for use with portable electronic dynamometers.

Clamp-on load cells have also been developed for use with portable electronic dynamometers. These load cells simply clamp around the polished rod and are quickly and easily installed or removed. These devices are generally known as extensiometers, measuring the strain of the polished rod with varying load. Because they are normally installed onto the polished rod with the rod already carrying a load, they do not measure the strain resulting from pre-existing load. Thus, the clamp-on load cells measure only relative load changes, not absolute loads. In order to measure absolute loads with the extensiometer-type load cell, the load, typically 5,000–10,000 pounds, must be taken off the polished rod prior to installation. This requires the use of additional equipment and people and the pumping unit must be stopped. Stopping of the pumping unit is undesirable because it may take several hours after restart before conditions again reach a steady state and allow any meaningful dynamometer readings to be taken.

SUMMARY OF THE INVENTION

Accordingly, an object of the present invention is to provide an improved sucker rod load measurement system which provides absolute readings of rod load without requiring that load be removed to establish zero.

Another object of the present invention is to provide a sucker rod load measurement system which may be installed by one person without special equipment and may be installed while the pumping unit is running.

According to the present invention, an improved sucker rod load measurement device includes at least one acoustic transducer for injecting an acoustic signal into a polished rod and at least one receiving transducer for detecting the injected signal and means for measuring the velocity of the signal in the polished rod. Variations in sucker rod load is determined from the variations in the acoustic signal velocity.

In a preferred embodiment, acoustic velocity is first measured in an unloaded portion of the polished rod to determine zero load conditions. Velocity measured in the loaded portion then provides an indication of the total load on the polished rod.

In a preferred embodiment the apparatus includes a single acoustic transmitter and two pairs of acoustic receivers. One pair of receivers is positioned on an unloaded portion of the polished rod string and the other is positioned on a loaded portion thereof. Acoustic velocity in the two portions of the rod is measured each time an acoustic impulse is applied to the rod and the difference between the two velocity readings indicates total instantaneous rod loading.

DESCRIPTION OF THE DRAWINGS

The present invention may be better understood by reading the following detailed description of the preferred embodiments with reference to the accompanying drawings wherein.

DESCRIPTION OF THE PREFERRED EMBODIMENT

Figure 1:
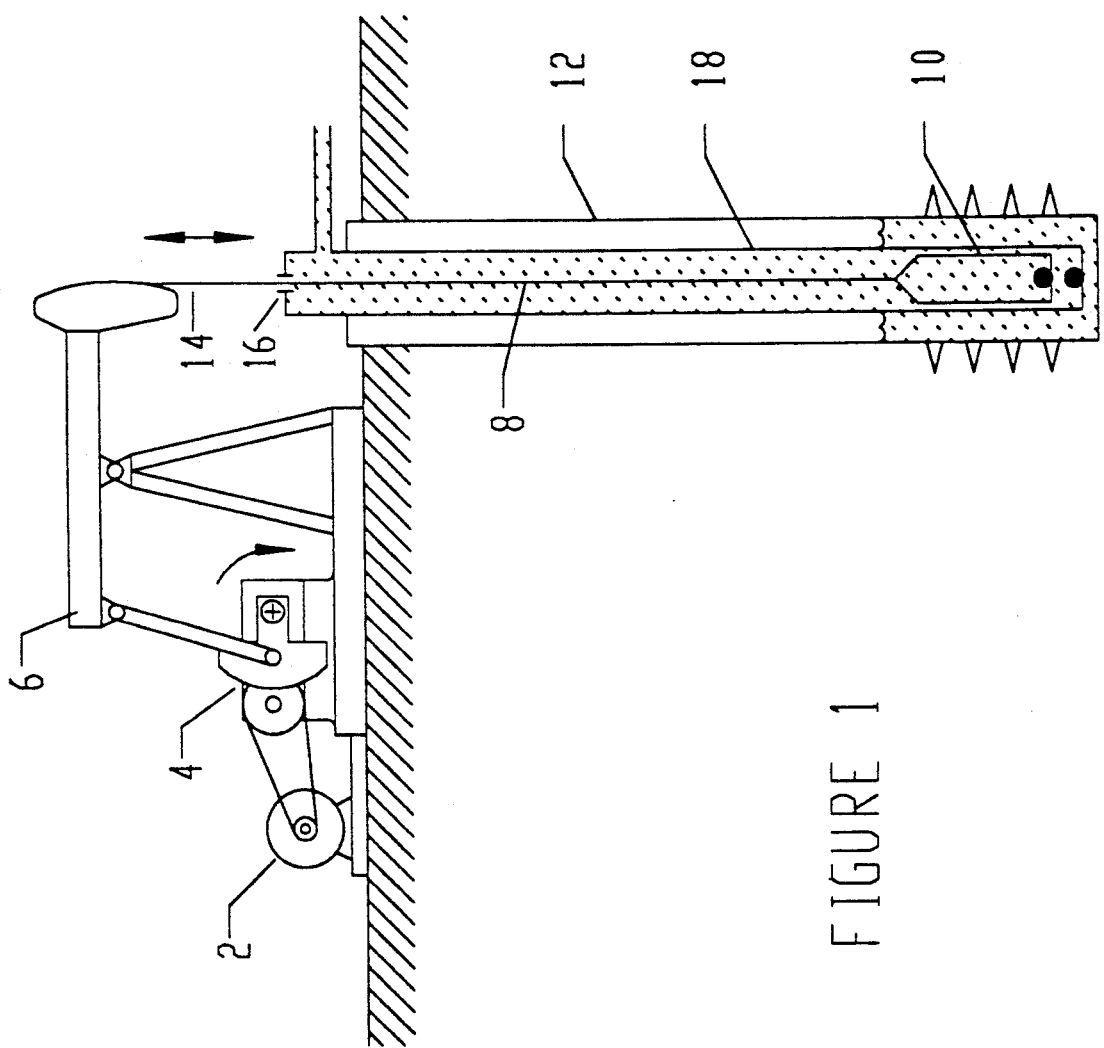
FIG. 1 is an illustration of a typical oil well sucker rod pumping system.
Figure 3:
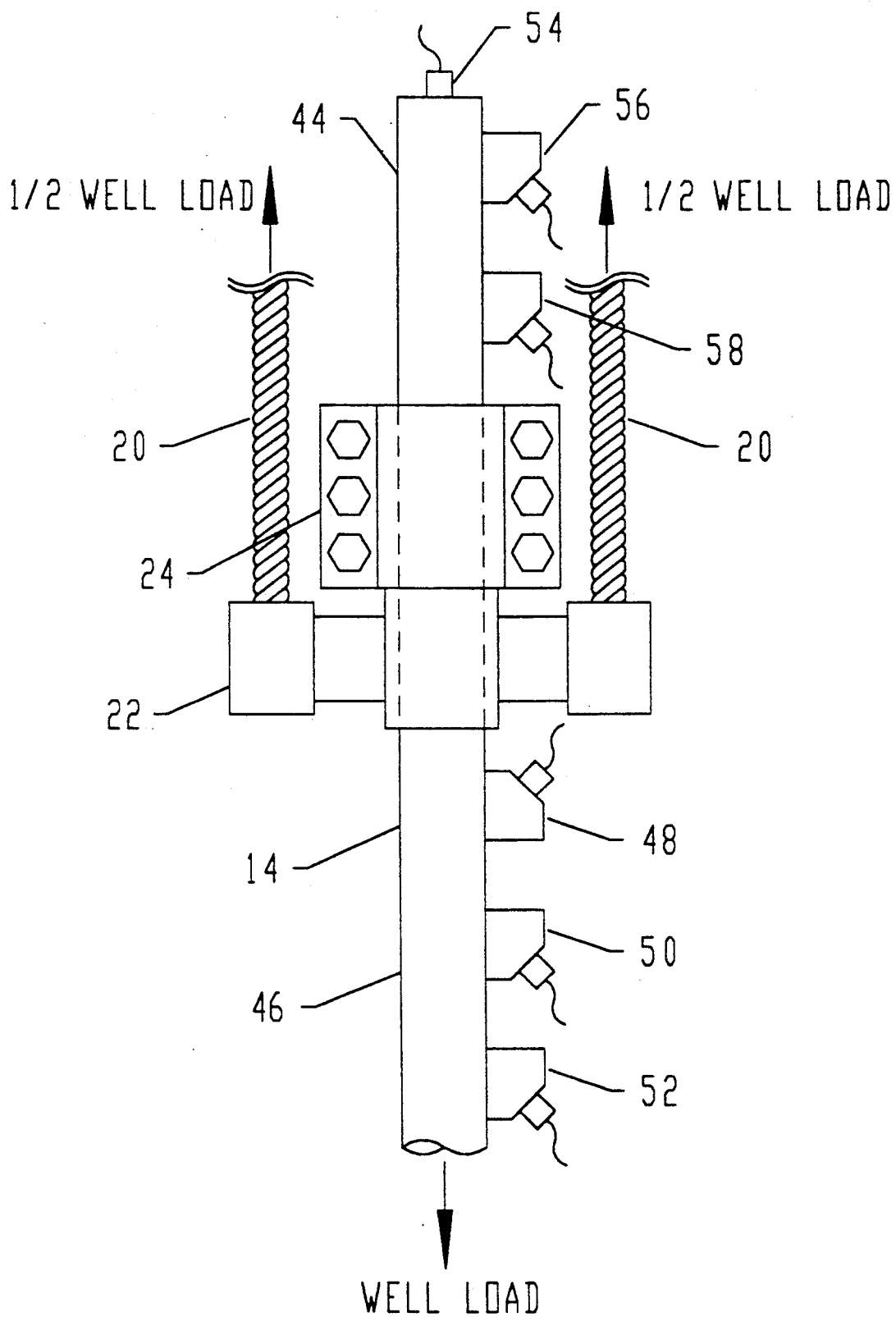
FIG. 3 is an illustration of the upper portion of a sucker rod string, its connection to the pumping unit wire line hanger, and the typical positioning of acoustic measuring devices thereon.

The basic components of a typical sucker rod pumping system are illustrated in FIG. 1 and discussed above. The primary input needed by a dynamometer is the total load on sucker rod string 8. The maximum loads on the sucker rod string 8 occur at its upper end 14 where it connects to the walking beam 6. This portion of the string is typically a polished steel rod portion designed to make a sliding fluid-tight seal with a packing 16 at the upper end of a tubing string 18. With reference to FIG. 3, the mechanical connection of the polished rod portion 14 to walking beam 6 is illustrated. Wire lines or cables 20 are connected to the polished rod by means of a carrier bar 22 and polished rod clamp 24. The wire lines 20 are connected on their upper ends to the walking beam 6.

The present invention is based on the fact that the speed of sound, or acoustic velocity, of a material varies in proportion to the amount of stress applied to the material and the fact that the sucker rod supporting system illustrated in FIG. 3 provides an unloaded or unstressed portion of the rod which may be used to provide a zero stress reference and thereby allow measurement of absolute stress in the loaded portion of the rod. The change of acoustic velocity with stress is known as the acoustoelastic effect and is a well-known phenomenon. Various attempts have been made to use this effect to determine stress levels in various metals. See, for example, the article entitled "Application of the Acoustoelastic Effect to Rail Stress Measurement" by D. M. Egle and D. E. Bray, Materials Evaluation, Mar. 1979, pages 41–46, 55 and the publication entitled "Using the Acoustoelastic Effect to Measure Stress in Plates", Davis M. Egle, Mar. 5, 1980, Lawrence Livermore Laboratory, Publication No. UCRL-52914 and available from the National Technical Information Service. Despite the experimental work which has been done with the acoustoelastic effect, no practical devices using the effect have been developed for a number of reasons. The greatest problem is that there normally is no stress-free or unloaded reference available. The acoustic velocity is also a function of metallurgy and thus can vary considerably between various samples of materials thought to be identical. In the present invention the problems are avoided by use of an unstressed portion of a polished rod as a zero reference where that unstressed portion is in close proximity to the stressed portion where load measurements are taken.

Figure 2:
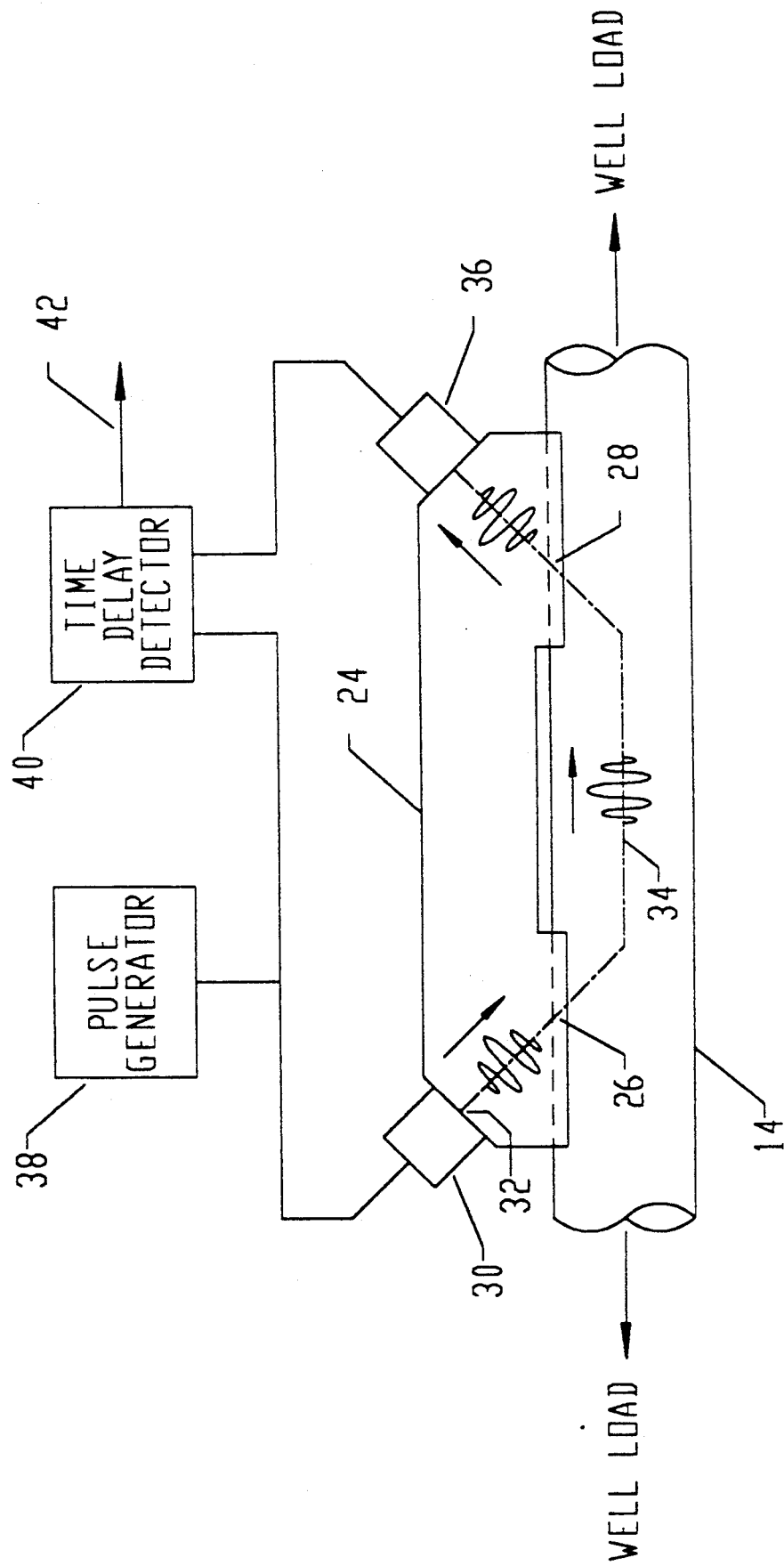
FIG. 2 is an illustration of a typical acoustic velocity measuring system according to the present invention.

With reference to FIG. 2, the basic operation of acoustoelastic effect velocity measurement is illustrated. In FIG. 2 a portion of the polished rod 14 is illustrated. A gauge block 24 is positioned in contact with the polished rod 14 at two points on its surface displaced by a known distance determined by the length of the gauge block. A transmitting transducer 30 is positioned on an appropriately inclined surface 32 of the gauge block for transmitting an acoustic pulses through the gauge block at the injection point 26 with the appropriate angle to generate a longitudinal wave as indicated by the ray path 34. A receiving transducer 36 is positioned on the opposite end of gauge block 24 to receive the sonic pulse after it is again refracted at receiving point 28.

An electronic pulse generator 38 provides the electrical signal to drive acoustic transducer 30. A time delay detector 40 receives the pulse from generator 3 and also receives the output of transducer 36 after the sonic pulse has traveled through polished rod 14. Detector 40 determines the time delay between the two pulses and provides the signal on output 42 which, together with the known distance between points 26 and 28, can be used to indicate acoustic velocity.

The acoustoelastic effect is expressed mathematically by the following equation:

$$V = V_0 (1 + Ks),$$

where, in the above subparagraph:
  $V$ = the speed of sound in a material under stress,
  $V_0$ = the speed of sound in the unstressed material;
  $K$ = the acoustoelastic constant of the material; and
  $s$ = the stress in the material For carbon steel, such as that used for manufacturing polished rod 14, the acoustoelastic constant K has a value of about $8.3 \times 10^{-8}$ per psi for longitudinal sound waves propagating parallel to the stress field. Minimum polished rod stress is typically about 3,000 psi. Therefore, to read the minimum stress to within 5% of its true value, that is, plus or minus 150 psi, the speed of sound must be measured to within 1 part in $10^5$. Commercially available time base measurement units are capable of reading appropriate time delays to within one part in $10^6$, offering the possibility of stress resolution as small as plus or minus 15 psi.

In one embodiment of the present invention, the gauge block system of FIG. 2 is used as a portable stress measurement device. The gauge block may be mechanically clamped to the polished rod 14 with an appropriate couplant such as grease filling the contact points between the gauge block and the polished rod. Alternatively, the gauge block 24 may include permanent magnets which provide sufficient force to hold the block in place on the polished rod. The gauge block may be first applied to the unstressed portion 44 of the polished rod, that is that part above polished rod clamp 24 as illustrated in FIG. 3. After recording a measurement of unstressed velocity, the gauge block may be moved to the stressed portion 46 of the polished rod 14 below the rod clamp 24. By using the above mathematical formula, together with instantaneous readings of stressed rod acoustic velocity, a dynamic load signal may be produced as an input to a diagnostic dynamometer system.

With further reference to FIG. 3, additional embodiments of the present invention are illustrated. On the stressed portion 46 of polished rod 14, there are illustrated three acoustic transducers comprising a single transmitting transducer 48 and two receiving transducers 50 and 52. Transducers 48, 50 and 52 may be mounted on a gauge block as illustrated on FIG. 2 if desired. In this embodiment the time delay measurement used to determine velocity is measured by determining the time delay between receipt of the acoustic signal at transducers 50 and 52. That is, transmitter 48 is used to inject an acoustic wave into the polished rod 14 which is then detected by both receivers 50 and 52. This arrangement avoids any uncertainty as to the actual points of injection and detection of the acoustic signal. Since receivers 50 and 52 may be identical, it may be safely assumed that the actual travel distance of signal through the polished rod 14 corresponds to the physical spacing between receivers 50 and 52.

On the unstressed portion 44 of polished rod 14, there is illustrated yet another arrangement of acoustic transducers. In this arrangement the transmitting transducer 54 is positioned on the upper end of polished rod 14 rather than on a typical wedge structure. Receiving transducers 56 and 58 may be identical to transducers 50 and 52 illustrated on the stressed portion 46. Transducer 54 may be used to inject a longitudinal acoustic signal into the polished rod 14 which will then be detected by detectors 56 and 58 for velocity determination.

If the system is to be permanently installed, it may be comprised of transmitting transducer 54 and receiving transducers 50, 52, 56 and 58. That is, transmitting transducer 48 would not be necessary since the impulses injected by transmitting transducer 54 will travel through the length of polished rod 14 and be detected sequentially by all four receiving transducers. This arrangement simplifies the overall system and allows measurement of a zero reference each time a stress measurement is taken on the loaded portion of the sucker rod. This arrangement would allow correction for all factors which affect acoustic velocity, such as temperature.

As described herein, the present invention uses longitudinal acoustic impulses, or pressure waves traveling parallel to the stress field. As is well known, the velocity of other acoustic wave forms is also affected by stress and may be used if desired. These wave forms include shear waves and surface waves. In addition, it should be possible to place an acoustic transmitter and receiver on opposite sides of the polished rod to detect velocity changes of a signal passing across rather than longitudinally down the axis of polished rod 14. However, due to the short path length, measurement accuracy would be lower. By using waves traveling longitudinally down the sucker rod, the distance, and, therefore, the time delay, may be increased if necessary to improve measurement accuracy. For this and other reasons, I believe the longitudinal pressure wave approach is preferred.

As indicated above, the gauge block 24 of FIG. 2 must be firmly coupled to the polished rod 14 and some form of couplant, such as grease or oil, must fill all space between the gauge block and the rod 14. As is well known, these steps are necessary to obtain good acoustic coupling for transmitting the acoustic wave forms into and receiving them from the rod 14. These problems can be overcome by use of a device known as an electromagnetic acoustic transducer or EMAT. These devices use an electromagnetic field to induce an acoustic wave into the surface of a metal part without the need for actual contact with the part. These devices are primarily effective for inducing a waveform having particle motion normal to the metal surface, such as a shear wave or surface wave. If desired, such EMATS may be used in place of the more typical acoustic transducers, provided the system is otherwise calibrated for the appropriate resulting waveform.

While the present invention has been illustrated and described with reference to the particular apparatus and methods of use, it is apparent that modifications may be made therein with in the scope of the invention as defined by the appended claims.

What is claimed is:

1. A method for measuring load on a sucker rod oil well pumping unit comprising:
    injecting an acoustic signal into a load-free portion of the sucker rod,
    measuring the time of travel of said signal between two points on said load-free portion of said sucker rod, said two points spaced apart by a preselected distance,
    injecting an acoustic signal into a load-bearing portion of said sucker rod,
    measuring the time of travel of said signal between two points on said load-bearing portion of said sucker rod, said two points spaced apart by a preselected distance,
    using said measured travel times to calculate the total load on said load-bearing portion of said sucker rod.

2. A method for measuring load on a sucker rod oil well pumping unit comprising:
    injecting an acoustic signal into said sucker rod,
    measuring the time of travel of said signal between two points on a load-free portion of said sucker rod, said two points spaced apart by a preselected distance,
    measuring the time of travel of said signal between two points on a load-bearing portion of said sucker rod, said two points spaced apart by a preselected distance,
    using said measured travel times to calculate the total load on said load-bearing portion of said sucker rod.

* * * * *